US010758131B2

(12) United States Patent
Olivier

(10) Patent No.: US 10,758,131 B2
(45) Date of Patent: Sep. 1, 2020

(54) NON-INVASIVE MEASUREMENT OF AMBULATORY BLOOD PRESSURE

(71) Applicant: LifeQ Global Limited, Dublin (IE)

(72) Inventor: Laurence Richard Olivier, Alpharetta, GA (US)

(73) Assignee: LifeQ Global Limited, Dublin (IE)

( * ) Notice: Subject to any disclaimer, the term of this patent is extended or adjusted under 35 U.S.C. 154(b) by 729 days.

(21) Appl. No.: 15/393,982

(22) Filed: Dec. 29, 2016

(65) Prior Publication Data

US 2017/0181641 A1 Jun. 29, 2017

Related U.S. Application Data

(60) Provisional application No. 62/272,238, filed on Dec. 29, 2015.

(51) Int. Cl.
*A61B 5/02* (2006.01)
*A61B 5/021* (2006.01)
*A61B 5/08* (2006.01)
*A61B 5/113* (2006.01)
*A61B 5/00* (2006.01)
A61B 5/024 (2006.01)

(52) U.S. Cl.
CPC ............ *A61B 5/021* (2013.01); *A61B 5/0816* (2013.01); *A61B 5/113* (2013.01); *A61B 5/6801* (2013.01); *A61B 5/7225* (2013.01); *A61B 5/7264* (2013.01); *A61B 5/7278* (2013.01); *A61B 5/742* (2013.01); *A61B 5/0022* (2013.01); *A61B 5/02416* (2013.01); *A61B 5/721* (2013.01); *A61B 5/7275* (2013.01); *A61B 2562/0219* (2013.01)

(58) Field of Classification Search
CPC ......... A61B 5/02; A61B 5/0205; A61B 5/021; A61B 5/7264; A61B 5/00; A61B 5/024; A61B 5/08; A61B 5/02405; A61B 5/02416; A61B 5/0816; A61B 5/14551; A61B 5/4035; A61B 5/7278; A61B 5/1073; G16H 50/20; G16H 40/63
USPC ................................ 600/301, 483, 500, 529
See application file for complete search history.

(56) References Cited

U.S. PATENT DOCUMENTS 4,754,761 A 7/1988 Ramsey, III et al.
5,776,071 A 7/1998 Inukai et al.
(Continued)

OTHER PUBLICATIONS

The PCT International Search Report and Written Opinion released by the U.S. Receiving Office dated Mar. 17, 2017; 8 pages.

*Primary Examiner* — Jon Eric C Morales
(74) *Attorney, Agent, or Firm* — Smith Gambrell & Russell LLP

(57) ABSTRACT

Systems and methods are provided in which data acquisition device detects and captures ambulatory radial arterial blood pressure in a non-invasive and continuous manner through the combined use of tonometry, accelerometry and photoplethysmography, together with the detecting and translating of Mayer waves. Transformed blood pressure data, together with motion and contextual data can be used as input for machine learning algorithms and biomathematical models which can predict the general state of health of an individual. Transformed blood pressure data, together with motion and contextual data, may be communicated via wireless communications to mobile devices and/or cloud based platforms.

14 Claims, 2 Drawing Sheets

(56) References Cited

U.S. PATENT DOCUMENTS

| | | |
|---|---|---|
| 7,001,337 B2 | 2/2006 | Dekker |
| 7,164,938 B2 | 1/2007 | Geddes et al. |
| 7,658,716 B2 | 2/2010 | Banet et al. |
| 8,216,136 B2 | 7/2012 | Addison et al. |
| 8,233,969 B2 | 7/2012 | Muhlsteff et al. |
| 2004/0260186 A1* | 12/2004 | Dekker ................ A61B 5/0205 600/483 |
| 2010/0228102 A1* | 9/2010 | Addison ............. A61B 5/0205 600/301 |
| 2014/0344208 A1 | 11/2014 | Ghasemzadeh et al. |
| 2015/0164349 A1 | 6/2015 | Gopalakrishnan et al. |
| 2017/0172433 A1* | 6/2017 | Olivier ................ A61B 5/0002 |

\* cited by examiner

NON-INVASIVE MEASUREMENT OF AMBULATORY BLOOD PRESSURE

CLAIM OF PRIORITY

The present application claims priority from Provisional Patent Application No. 62/272,238, filed on Dec. 29, 2015, the disclosure of which is relied upon and incorporated herein in its entirety by reference.

FIELD OF INVENTION

The present invention relates to the field of non-invasive digital health monitoring and physiological signal processing. In particular, systems and methods to detect ambulatory blood pressure in an accurate, non-invasive, and continuous manner are presented.

BACKGROUND

The term "blood pressure" (BP) is defined as the pressure that is exerted upon the walls of arterial blood vessels due to blood circulating. BP is measured in millimeters of mercury (mm Hg) and is expressed in terms of the systolic pressure/diastolic pressure of the heart, e.g. 120/80 mm Hg. Systole is the part of the cardiac cycle when the ventricles contract and blood is forced outwards into the arteries. This results in the maximum pressure within the arterial blood stream occurring during each contraction, or beat, of the heart. Systole is followed by diastole, during which the atria dilate and the ventricles relax and refill with blood during the period between heartbeats. Diastole results in the minimum pressure within the arterial blood stream occurring during each heartbeat. A normal blood pressure value lies at or below 120/80 mm Hg, and is a result of sufficient arterial wall elasticity in the larger arteries and no fluctuation in the width of smaller blood vessels.

Abnormal blood pressure values are a fundamental diagnostic factor in the identification of conditions of the cardiovascular system, and are also indicative of endocrine and/or neurological disorders. Considering the effects of abnormal blood pressure vary from acute and potentially dangerous symptoms such as dizziness and/or fainting to chronic and life-threatening end-organ cardiac and renal damage, all effects of abnormal blood pressure levels are significant.

In 2014, approximately 22% of adults aged 18 and over had elevated blood pressure levels, or hypertension, globally. In the USA alone, approximately 29% of adults suffer from hypertension, of which only about 50% manage the condition effectively. At present, hypertension is the dominant cause of stroke and kidney failure and is part of a greater disease cluster continually accompanied by obesity, diabetes, kidney disease or many other co-existing problems involving lifestyle and/or genetics. Since high blood pressure is often not associated with noticeable symptoms, one in five adult individuals afflicted is unaware of it, with the cost of the condition to the United States amounting to roughly US$46 billion yearly. In 2013, more than three hundred sixty thousand deaths with high blood pressure as the principal or participating cause were recorded. Therefore, early detection, before high blood pressure leads to serious conditions, is essential.

Notwithstanding the fact that a currently used method for the accurate, direct, and continuous measurement of blood pressure exists, the method is invasive (it entails the use of an intravascular canula needle) and limited (potential complications such as thrombosis, bleeding and infection can arise). Also, for most individuals, obtaining a blood pressure reading with subsequent diagnosis necessitates a doctor's or clinic appointment, which can be time-consuming, costly and/or logistically demanding (for example in rural areas).

BP can be measured from different locations on or within the body, as well as different arteries, the methods varying in accuracy and feasibility. Reasons for utilizing different locations vary from accuracy of the method used on a specific artery, accessibility of an artery (for example, patients who are undergoing cardiac catheterization surgery are the only candidates for the most accurate, yet most invasive method, which involves measuring BP from the aortic root), as well as the type of equipment to which a clinic/hospital/medical officer has access. Currently, the most accurate non-invasive method is to measure brachial blood pressure (bBP). However, as bBP involves placing an inflatable cuff on the upper arm, it is not suitable for individuals who are sensitive to pressure and discomfort, such as the elderly, or persons with wounds or skin ailments in the area.

An alternative method, which is non-invasive and poses no pain or discomfort, is to perform tonometry of the radial artery (RA). The RA runs distally on the anterior part of the forearm, with the radial pulse measured from the wrist, in front of the distal end of the radius, where the RA lies superficially. Tonometry entails the use of a strain gauge pressure sensor exerting mild pressure over an artery. Subsequently, the artery is partially flattened and the arterial pressure is transmitted from the artery to the sensor, after which signal processing takes place to produce a digital readout.

Low-frequency arterial pressure fluctuations, termed Mayer waves, also occur due to sympathetic nervous system activity. Oscillations, or vibrations, in pressure receptor and chemo receptor reflex control systems generate these waves in arterial BP. Mayer waves occur spontaneously as a result of oscillation of the sympathetic vasomotor tone, and are detected through the application of spectral techniques to simultaneously recorded arterial pressure and efferent sympathetic nervous activity. It is speculated that Mayer waves trigger the release of endothelium-derived nitric oxide through cyclic changes in vascular shear stress, which could be beneficial to end organ function. Mayer waves can be measured by means of either tonometry, a photoplethysmography (PPG) sensor, or both. The short-term changes in blood volume are translated into pulse rate, and using tonometry in combination with PPG data mediates the filtering of the pressure wave signal for greatly enhanced accuracy and signal clarity after signal processing.

Two currently used gold standard measurements for BP exist. However, the first method is accurate, yet invasive, while the second method is non-invasive, yet less accurate. The first method entails direct measurement of aortic root pressures by passing a pressure transducer connected to a catheter directly into the aortic root at the time of cardiac catheterization. However, due to the high level of invasiveness of this method, it is not suited for routine clinical practice. The second method entails analysis of the radial artery waveform, obtained by non-invasive tonometry. The radial waveform is usually calibrated to bBP, measured using a brachial cuff and oscillometric devices, thereby generating a calibrated radial artery pressure waveform. However, this method presents challenges regarding a) accuracy, due to the phenomenon of white-coat hypertension and b) continuity, as the patient has to schedule an appointment to have BP measured. Moreover, during the implementation of both of the gold standard BP measuring methods, it is imperative that the subject remain still.

The inventors hereby recognized that the existing mechanisms used to measure BP are exclusive with regards to accuracy and/or invasiveness and/or discomfort to the user. Therefore, a strong need exists for a mechanism to measure ambulatory BP, i.e. to measure BP as the subject moves around, executing normal daily activities, in a non-invasive, accurate and continuous manner, simultaneously. Further, such mechanism needs to be non-invasiveness, accurate and continuous) for determining ambulatory BP.

SUMMARY OF THE INVENTION

The claimed invention aims to provide systems and methods to measure accurately ambulatory blood pressure (BP) in a non-invasive and continuous manner. The systems and methods described herein are employed simultaneously, together with detection means and translation of observed Mayer waves, to obtain BP values. In an aspect, the claimed invention utilizes a data acquisition device to carry out the ambulatory BP measurement. In an aspect, the data acquisition device detects and processes BP values continuously and/or periodically in real time. In an aspect, the data acquisition device communicates via wireless communication means the generated BP data streams to external computing devices and/or cloud-based platforms, where BP-related data may serve as input for machine learning algorithms and/or modeling to predict the general state of health of an individual.

In an aspect, the data acquisition device is configured to be attached to the body of the subject. The attachment means can include, but are not limited to, a wrist strap, chest strap, upper arm strap, or implant. In an aspect, the data acquisition device utilizes an accelerometer, a pressure sensor, a hermetically sealed capsule, and a PPG sensor simultaneously, together with Mayer wave detection and translation, to obtain BP readings. In an exemplary aspect, the acquisition device, attached to the subject at the wrist, uses a hermetically sealed medium (i.e., gas/fluid/gel) filled capsule coupled to a differential pressure sensor (e.g., MP3V5050) through which different pressures exerted by the radial artery on the differential pressure sensor are translated back to a blood pressure reading (systolic/diastolic). The capsule is positioned over the radial artery, after which sensor output is passed through an amplification circuit and, thereafter, to an analog to digital (AD) converter. The pressure sensor can be employed in combination with either an accelerometer, to measure the level of activity, or a pulse oximeter to generate photoplethysmography (PPG) signals, or the combination of both an accelerometer and pulse oximeter, to increase the clarity of the signal and enhance accuracy of the raw, and subsequently, processed data.

In an aspect, the data acquisition device is configured for continuous detection, capturing, and processing of radial arterial pulse pressure signals into BP data streams. In an aspect, said data acquisition device communicates via wireless means the BP data streams to external computing devices and/or cloud-based platforms, where BP-related data may serve as input for machine learning algorithms and/or modeling to predict the general state of health of an individual. In an aspect, data is transferred via wireless communications to computing devices including, but not limited to, smartphones, personal computers, laptop computers, tablets, and various other computing devices with an internet connection that communicate with a cloud-based platform. In other aspects, the data acquisition device is in direct communication with the cloud-based platform.

In an aspect, the BP data is used as input for machine learning algorithms and/or biomathematical models to predict the general state of health of an individual. In an aspect, the machine learning algorithms and models can be found on various computing devices, including, but not limited to, the cloud-based platform, mobile devices, personal computers, and on the data acquisition device itself. In an aspect, the algorithms and models generate quantified health metrics that are relayed back through wireless communications, from said cloud-based platform, to mobile devices and/or the data acquisition device, where it is displayed and/or notified to the user. Also, in particular embodiments, quantified health metrics may be relayed to third party databases such as, but not limited to, clinical parties, health insurance and retail parties.

These and other aspects of the invention can be realized from a reading and understanding of the detailed description and drawings.

DETAILED DESCRIPTION AND DRAWINGS

The present invention is directed at systems and methods that accurately measure ambulatory blood pressure (BP) in a non-invasive and continuous manner. In an aspect, these systems and methods use tonometry, accelerometry and photoplethysmography, together with the detecting and translating of Mayer waves, to measure the ambulatory BP of the subject. The systems and methods can utilize wireless communications means to provide obtained ambulatory BP measurement data to mobile devices and/or cloud-based platforms, where BP data can serve as input for algorithm processing, biomathematical modeling, and general state-of-health inferences and predictions.

Figure 1A:
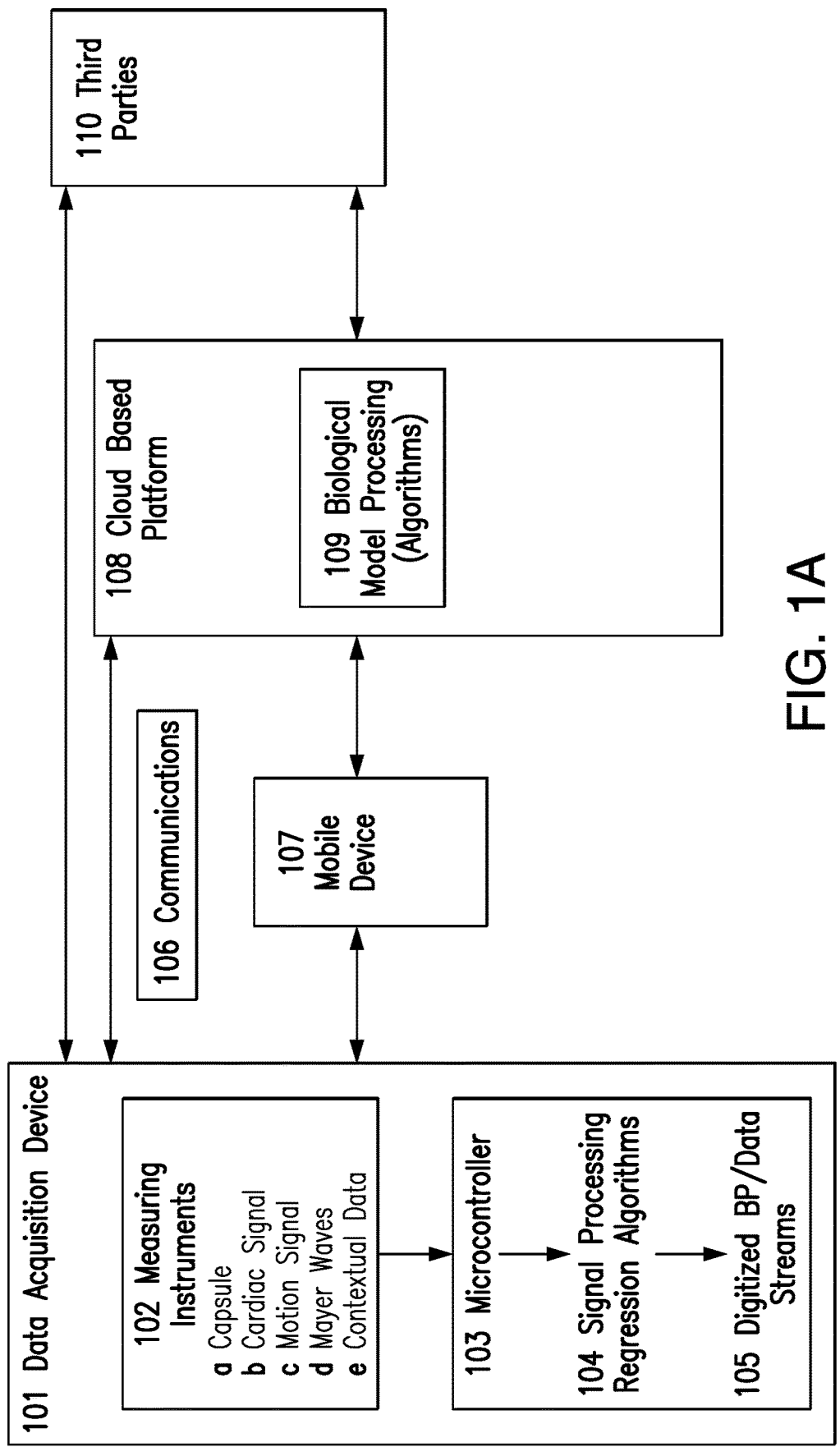
FIG. 1A is a schematic representation of the preferred embodiment in the form of a wearable device used for measuring, processing, relaying, and displaying blood pressure values data of a user in real time.

In an aspect, the claimed invention utilizes a data acquisition device 101 to carry out the ambulatory BP measurement. In an aspect, the data acquisition device 101 detects and processes BP values continuously and/or periodically in real time. Heartbeats induce pressure changes in the surrounding subcutaneous tissue. As the heart beats continuously, these changes travel down the length of the arm and, in particular, the radial artery, as radial pulse waves. As illustrated in FIG. 1A, the data acquisition device 101 measures ambulatory radial arterial BP from the wrist, chest, upper arm, or as an implant, in a non-invasive and continuous manner. In an aspect, the data acquisition device 101 measures ambulatory radial arterial BP from the wrist, chest, upper arm, or as an implant, in a non-invasive and continuous manner. In an exemplary aspect, the data acquisition device 101 includes measuring instruments 102 to measure the ambulatory BP. In an aspect, the measurement instruments include a capsule 102(*a*), a differential pressure sensor 102(*b*) that can create a cardiac signal, a motion sensor 102(*c*) configured to make a motion signal and Mayer wave sensors 102(*d*) (e.g., a PPG sensor). The device 101 can also use contextual data 102(*e*) about the subject (e.g., known medical history, diet, etc.), which can be provided directly by the subject or acquired through other means.

In an aspect, the capsule 102(*a*) is in contact with the differential pressure sensor 102(*b*). In an exemplary aspect, the capsule 102(*a*) is a hermetically sealed medium (gas/fluid/gel) filled capsule 102(*a*) positioned in the closest possible contact with the radial artery in order to detect the radial pulse wave generated by blood flow within the artery of the subject. The medium can comprise various gases and fluids. Further, the capsule 102(*a*) can be comprised of a highly elastic material that is impermeable to the fluids and gases contained within. Consequently, energy from each wave is transferred from the surface of the capsule 102(*a*) to the medium within (i.e., the gas/fluid/gas) and passed on to the pressure sensor 102(*b*). The pressure sensor 102(*b*) can then capture heart beat fluctuations.

The pressure sensor 102(*b*) converts the energy into a signal transferred to a microcontroller 103 within the data acquisition device 101. The signal is then decoded, filtered, and manipulated into a digitized BP measurement and/or data streams 105 by means of signal processing and regression algorithms 104. The data streams can indicate low, normal, and/or high frequency heart beat fluctuations, mean pressure, and the like.

As previously described, low-frequency arterial pressure fluctuations, termed Mayer waves, can also be seen as useful perturbations to measure BP. Oscillations, or vibrations, in pressure receptor and chemo receptor reflex control systems generate these waves in arterial BP. Mayer waves occur spontaneously, and result from an oscillation of the sympathetic vasomotor tone. It is speculated that Mayer waves trigger the release of endothelium-derived nitric oxide through cyclic changes in vascular shear stress, which could be beneficial to end organ function. Mayer waves can be detected by the Mayer wave sensors 102(*d*). In an aspect, such sensors 102(*d*) can include a photoplethysmography (PPG) sensor 102(*d*) or use tonometry (i.e., the differential pressure sensor 102(*b*)), or both. The Mayer wave sensors 102(*d*) can also translate the wave into signals that can be decoded, filtered, and manipulated, as discussed above.

In addition, the data acquisition device 101 can also employ motion sensors 102(*c*). The motion sensors 102(*c*) can include accelerometers, gyroscopes, and the like. The motion sensors 102(*c*) pass along signals indicating the activity and the breathing rate of the subject. Such information is passed along with other data in order for the health diagnosis to be more robust (e.g., the breathing rate can be used to correct heart stroke volume).

The detected signals are translated into pulse rate, and using PPG data in combination with tonometry data mediates the filtering of the pressure wave signal for greatly enhanced accuracy and signal clarity after signal processing. For example, when variations in PPG signals caused by changes in the heart stoke volume occur, the data is compensated by taking into account the change through breathing rate. In an aspect, direct measurement is performed by the motion sensor 102(*c*), or through indirect measurement such as heart beat interval variation due to sinus arrhythmia. The manner in which the pressure signal in the radial artery is translated into readings in the pressure signal can be labeled a transfer function. In an aspect, the transfer function is used to map changes in the AC and DC components of the signal at more than one pressure value to the systolic/diastolic/mean arterial BP of the subject. However, removal and reattachment of the data acquisition device 101, including the measuring instruments 102, by the user poses a significant challenge, as the signal taken in different spatial/orientation contexts cannot be compared. This technique solves this problem by exploiting the naturally occurring Mayer—pressure waves, which occur on a time scale of ~13 seconds, and can be recorded in a single spatial context to obtain near continuous measurement of BP.

In particular embodiments, digitized BP data 105 obtained from either the pressure sensor 102(*b*), PPG sensor 102(*c*) or tonometry 102(*d*) (e.g., an accelerometer), or a combination thereof, is converted into a user-friendly readout, and can be directly displayed on the data acquisition device 101 (e.g., a display or screen). In other embodiments, digitized BP data may be wirelessly communicated 106 from the data acquisition device 101 to another computing device 107, exemplified by, but not limited to, smartphones, tablet and laptop computers for display. In addition, digitized BP data and/or readouts may also be communicated 106 from said computing devices to cloud-based platforms 108. In other embodiments, digitized BP data is transmitted directly from the data acquisition device to a cloud-based platform.

In an aspect, digitized BP data 105 serves as an input for cloud-based biological model processing 109. The biological model processing 109 can use various algorithms to create biomathematical models. Models of the human cardiovascular system derived from the scientific literature and combined or developed further in-house can be used to interpret the physiological signals measured by the data acquisition device 101 in order to infer the most likely underlying physiological condition of the subject, which may include health or disease states. Model outputs 109 may include, but are not limited to, general state of health prediction, and/or the probability of the occurrence of a clinical condition directly related to abnormal blood pressure. For example, the relationship between low frequency arterial pressure fluctuations to high frequency heart beat fluctuations along with mean pressure can be used to determine various health values related to BP. For example, such health values can reflect, but are not limited to, systolic, diastolic, and mean atrial BP values. These values then are used to state the health status of the subject.

In some aspects, BP-derived metrics and modeled state-of-health predictions are relayed to third parties 110. In an aspect, this information is only shared with third parties 110 upon receiving consent from the subject. In an aspect, the third parties 110 include, but are not limited to, clinical, insurance and retail parties. These third parties 110 can then store such information in various databases for later access. Moreover, said metrics and predictions generated from the modeling 109 are relayed back to the data acquisition 101 and/or mobile device 107 of the user for display on the device interface, and/or as notification to the user.

Figure 1B:
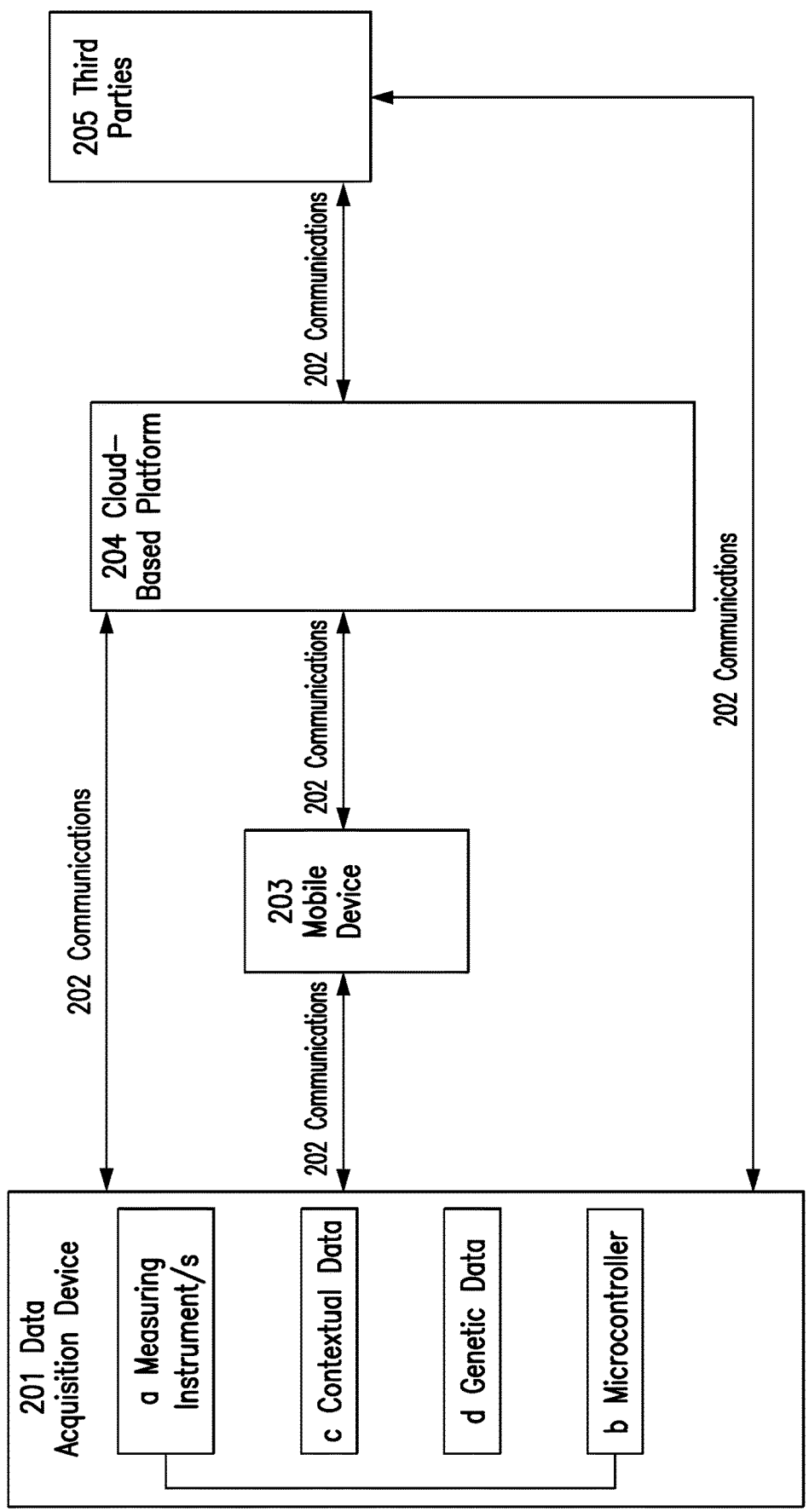
FIG. 1B is a schematic representation illustrating the modules by which the described systems and methods operate, together with the flow of information with regards to device communication.

FIG. 1B is a schematic representation of the data acquisition device 201 in combination with wireless communications 202 to mobile devices 203, a cloud-based platform 204, and third parties, exemplified by clinical and insurance parties 205, illustrating the flow of information between devices. The data acquisition device 201 includes at least one measuring instrument 201(*a*) measuring radial arterial pulse pressure, at least one microcontroller 201(*b*) capable of processing said signals into digitized readouts, while directly communicating 202 said data to a cloud-based platform 204 or mobile device 203 connected to a cloud-based platform 204, both through wireless internet connections 202. Contextual data 201(*c*) entered by the user, exemplified by, but not limited to, details regarding previously diagnosed diseases, e.g. diabetes and details regarding behavioral habits, e.g. smoking, together with genetic data 201(d), as well as data collected by the data acquisition device 201, serve as input for state-of-health prediction model processing on the cloud-based platform 204. Quantified metrics can be relayed from the cloud-based platform to the user, or can be accessed by third parties 205, exemplified by, but not limited to, clinical, insurance and retail parties, via internet communications 202.

USER EXAMPLE

Diabetes leads to several secondary health risks, of which serious and irreversible blood vessel damage, caused by insulin resistance and/or the lack of insulin, is inevitable. The nature of this damage renders blood vessels susceptible for atherosclerosis, which in turn leads to hypertension. Should the individual be unaware of being hypertensive, as is frequently the case when continuous BP monitoring is not possible, eye disease, kidney failure, stroke, heart failure and/or heart attack could follow. Therefore, in order to prevent specific diabetes complications, it is imperative for diabetics to be able to measure ambulatory BP accurately and continuously, which in turn will mediate early diagnosis and subsequent intervention against life-threatening complications.

In one embodiment of the invention, a wrist-based data acquisition device 101 collects physiological signals via a PPG sensor 102(c), motion sensor 102(d), and pressure sensor 102(b) in contact with a hermetically sealed medium (gas/fluid/gel)-filled capsule 101(a), from a wearer. Prior to activating the device 101 for measuring said signals, the wearer provides contextual information 102(e) for health monitoring via interaction with the device interface—either directly on the device 101, or through a mobile device 107 connected to the wearable device 101 via a wireless connection 106. Contextual information is exemplified by, but not limited to, sex, age, body mass, level of activeness (for example, sedentary up to vigorously active on a scale of 0 to 5) and pre-diagnosed conditions such as diabetes or atherosclerosis. Any and all information logged onto the device 101 is transmitted to the cloud based platform 108, and, the more comprehensive the initial context provided by the user, the more accurate and relevant the feedback that can be provided. The contextual data 102(e) and biological metrics 105 generated by the signal processing component 104 can also be accessed by third parties 110 through an allocated database and/or a mobile device 107, in order to make physiological and environmental (for example, lifestyle) inferences to aid in providing the user with relevant guidelines as to general state of health. Inference can be presented as very healthy (zero to little risk of clinical pathology with zero to little requirement for lifestyle changes) moderately healthy (needs to make minor lifestyle changes), or unhealthy (imminent pathological condition, which warrants immediate medical intervention). Upon continuous use of the invention, state-of-health predictions diagnostic tools can attain optimum accuracy, to the point of being exploited as a diagnostic tool.

Having thus described exemplary embodiments of a method to capture ambulatory blood pressure data, it should be noted by those skilled in the art that the within disclosures are exemplary only and that various other alternatives, adaptations, and modifications may be made within the scope of this disclosure. Accordingly, the invention is not limited to the specific embodiments as illustrated herein, but is only limited by the following claims.

What is claimed:

1. A method to provide an estimate of blood pressure of a subject, comprising:
    a) using as input, a plurality of signals containing degrees of cardiac activity and motion data of the subject, including low-frequency arterial pressure fluctuations (Mayer waves), wherein at least the Mayer waves are captured using tonometry;
    b) processing the plurality of signals to form blood pressure data; and
    c) applying modeling to the blood pressure data to determine the estimated blood pressure of the subject.

2. The method of claim 1, wherein the plurality of signals further comprises radial arterial pulse pressure and high frequency heart beat fluctuations.

3. The method of claim 2, wherein the Mayer waves are further captured using photoplethysmography.

4. The method of claim 2, wherein the plurality of signals further comprises motion signals that represent an activity rate and a breathing rate of the subject.

5. The method of claim 1, wherein the estimated blood pressure of the subject comprises an estimate of systolic and diastolic blood pressure of the subject.

6. The method of claim 1, wherein the estimated blood pressure of the subject comprises an estimate of mean arterial blood pressure of the subject.

7. The method of claim 1, further comprising acquiring contextual data about the subject and using the contextual data with the blood pressure data.

8. The method of claim 7, wherein the contextual data comprises medical and genetic data of the subject.

9. The method of claim 1, further comprising using the estimated blood pressure of the subject to infer a physiological condition of the subject.

10. The method of claim 1, wherein the blood pressure data and the estimated blood pressure are formed by a data acquisition device.

11. The method of claim 10, wherein the data acquisition device comprises a wearable device.

12. The method of claim 11, wherein the data acquisition device is configured to display the estimated blood pressure to the subject.

13. The method of claim 10, wherein the data acquisition device is configured to wirelessly transmit the blood pressure data and the estimated blood pressure to other devices.

14. The method of claim 1, wherein steps a-c are repeated continuously to provide continuous estimated blood pressure for the subject.

* * * * *